United States Patent [19]

Musser et al.

[11] Patent Number: 4,904,786
[45] Date of Patent: Feb. 27, 1990

[54] QUINOLINE COMPOUNDS AS ANTIALLERGIC AND ANTIINFLAMMATORY AGENTS

[75] Inventors: John H. Musser, Malvern; Dennis M. Kubrak, Drexel Hill; Anthony F. Kreft, III, Trooper; Reinhold H. W. Bender, Valley Forge, all of Pa.

[73] Assignee: American Home Products Corporation, New York, N.Y.

[21] Appl. No.: 231,130

[22] Filed: Aug. 11, 1988

Related U.S. Application Data

[60] Continuation-in-part of Ser. No. 50,595, May 15, 1987, Pat. No. 4,772,703, which is a continuation-in-part of Ser. No. 823,163, Jan. 27, 1986, Pat. No. 4,675,405, which is a continuation-in-part of Ser. No. 787,939, Oct. 16, 1985, abandoned, which is a division of Ser. No. 653,733, Sep. 21, 1984, Pat. No. 4,581,457.

[51] Int. Cl.$^4$ ............................................. C07D 215/00
[52] U.S. Cl. ..................................... 546/152; 546/176
[58] Field of Search ........................ 546/152, 153, 176

[56] References Cited

U.S. PATENT DOCUMENTS

| | | | |
|---|---|---|---|
| 4,625,035 | 11/1986 | Neiss | 546/152 |
| 4,631,287 | 12/1986 | Chakraborty et al. | 546/153 |
| 4,661,499 | 4/1987 | Young | 546/152 |
| 4,675,405 | 6/1987 | Musser et al. | 546/153 |
| 4,681,940 | 7/1987 | Musser | 546/176 |
| 4,732,978 | 3/1988 | Kreft | 540/152 |
| 4,738,710 | 4/1988 | Serban | 546/153 |
| 4,769,461 | 9/1988 | Musser et al. | 546/152 |
| 4,772,703 | 9/1988 | Musser et al. | 546/152 |
| 4,778,931 | 10/1988 | Musser | 546/152 |
| 4,794,188 | 12/1988 | Musser et al. | 546/152 |
| 4,839,369 | 6/1989 | Youssefyeh | 546/152 |

OTHER PUBLICATIONS

Chemical Abstracts vol. 109, entry 37743q.
Chemical Abstracts vol. 109 entry 110271r abstracting German OLS 3,632,329 (1988).

Primary Examiner—Donald G. Daus
Attorney, Agent, or Firm—George Tarnowski

[57] ABSTRACT

There are disclosed compounds of the formula

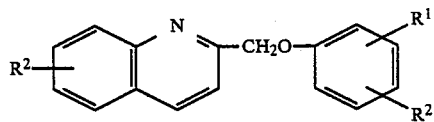

wherein R$^1$ is

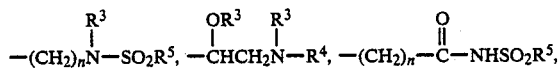

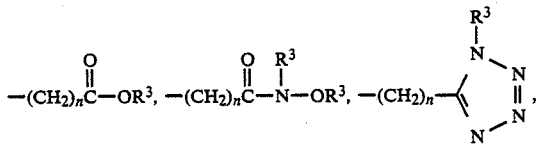

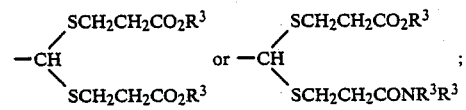

n is 0–5;
R$^2$ is hydrogen, loweralkyl, loweralkoxy, lower alkoxycarbonyl, trifluoromethyl, nitro, cyano or halo;
R$^3$ is hydrogen or loweralkyl;
R$^4$ hydrogen, lower alkyl, —COOR$^3$ or

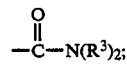

R$^5$ is lower alkyl, monofluoroloweralkyl, difluoroloweralkyl, polyfluoroloweralkyl, perfluoroloweralkyl or

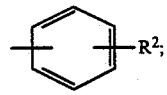

and the pharmaceutically acceptable salts thereof, and their use in the treatment of leukotriene-mediated nasobronchial obstructive airpassageway conditions, such as allergic rhinitis, allergic bronchial asthma and the like, and as antiinflammatory agents.

3 Claims, No Drawings

QUINOLINE COMPOUNDS AS ANTIALLERGIC AND ANTIINFLAMMATORY AGENTS

This is a continuation-in-part of U.S. Ser. No. 050,595, filed May 15, 1987, now U.S. Pat. No. 4,772,703, which is a continuation-in-part of U.S. Ser. No. 823,163, filed Jan. 27, 1986, now U.S. Pat. No. 4,675,405, issued June 23, 1987, which is a continuation-in-part of U.S. Ser. No. 787,939, filed Oct. 16, 1985, and now abandoned, which is a divisional of U.S. Ser. No. 653,733, filed Sept. 21, 1984, now U.S. Pat. No. 4,581,457.

This invention relates to novel heterocyclic compounds possessing lipoxygenase inhibitory and leukotriene antagonist activity, which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.* 215, 115–118 (1980); *Biochem. Biophys. Res. Commun.* 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent broncho-constrictors of the human bronchi [see Dahlen et al., *Nature* 288, 484–486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al., *Prostaglandins,* 23, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831–833 (1981)], which stimulates cell accumulation and affects vascular smooth muscle [see Bray, *Br. Med. Bull.*, 39, 249 (1983)]. The activity of leukotrienes and mediators of inflammation and hypersensitivity is extensively reviewed in Bailey and Casey, *Ann. Reports Med. Chem.*, 17, 203–217 (1982) and in Bray, *Agents and Actions,* 19, 87 (1986).

Accordingly, the biological activity of the leukotrienes and SRS's and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or antagonizing their affects. Thus, compounds which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula

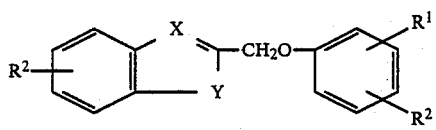

wherein
X is

or —N═;
Y is

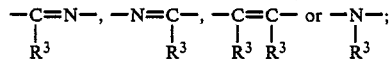

$R^1$ is

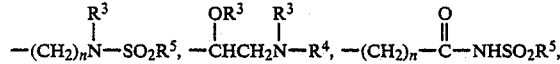

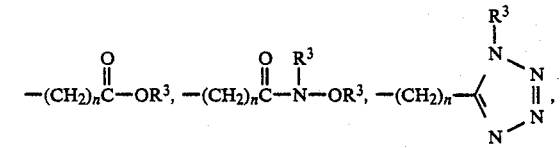

n is 0–5;
$R^2$ is hydrogen, loweralkyl, loweralkoxy, lower alkoxycarbonyl, trifluoromethyl, nitro, cyano or halo;
$R^3$ is hydrogen or loweralkyl;
$R^4$ is hydrogen, lower alkyl, —COOR$^3$ or $$-\overset{O}{\underset{\|}{C}}-N(R^3)_2;$$

$R^5$ is lower alkyl, monofluoroloweralkyl, difluoroloweralkyl, polyfluoroloweralkyl, perfluoroloweralkyl or

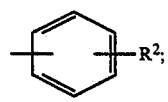

and the pharmaceutically acceptable salts thereof.

The term "halo" refers to fluoro, chloro, and bromo. The terms "loweralkyl" and "loweralkoxy" refer to moieties having 1–6 carbon atoms in the carbon chain.

The compounds of the invention can be prepared via variants of a basic reaction scheme using appropriate starting materials. Thus, compounds in which $R^1$ is the moiety

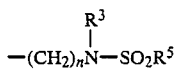

can be prepared by the reaction of an appropriate aniline derivative with an appropriate alkyl sulfonyl chloride or alkyl sulfonic anhydride as follows:

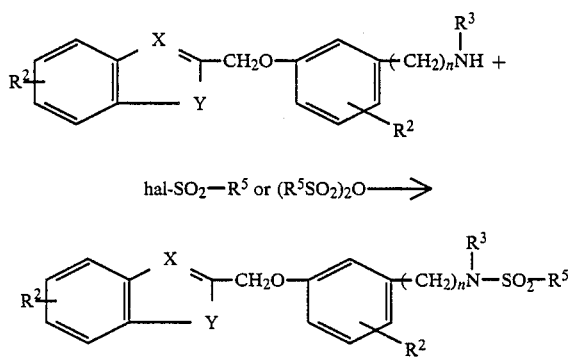

where X, Y, $R^2$, $R^3$, $R^5$ and n are as defined hereinbefore and hal refers to a halo radical, for example, chloro or bromo. The reaction is carried out in an organic solvent, for instance tetrahydrofuran, and at room temperatures. The starting aniline derivatives employed in this reaction sequence can be prepared as follows:

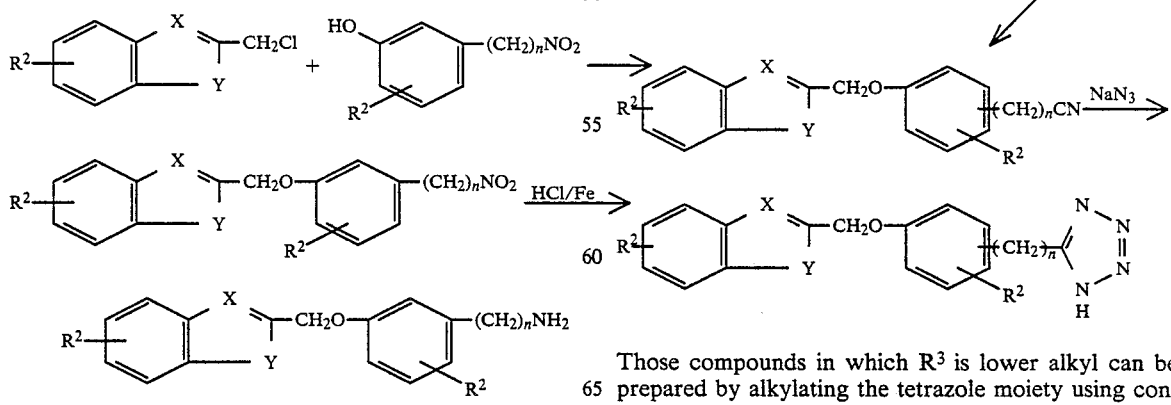

Additionally, those compounds in which $R^1$ is the moiety

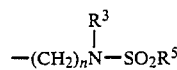

and $R^3$ is lower alkyl, can be readily prepared from the compounds wherein $R^3$ is hydrogen by the following reaction sequence:

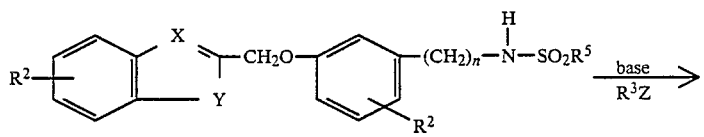

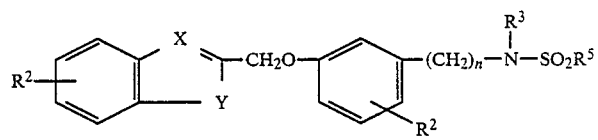

wherein X, Y, $R^2$, $R^3$, $R^5$ and n are as defined hereinbefore and Z is the replaceable portion of the alkylating agent $R^3Z$, which can be any of the conventional alkylating agents, such as for example the alkyl halides, alkyl sulfates, alkyl sulfonates and so forth.

Compounds of the invention in which $R^1$ is

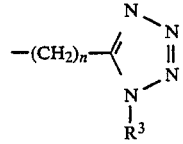

and $R^3$ is hydrogen, can be prepared by the following reaction scheme:

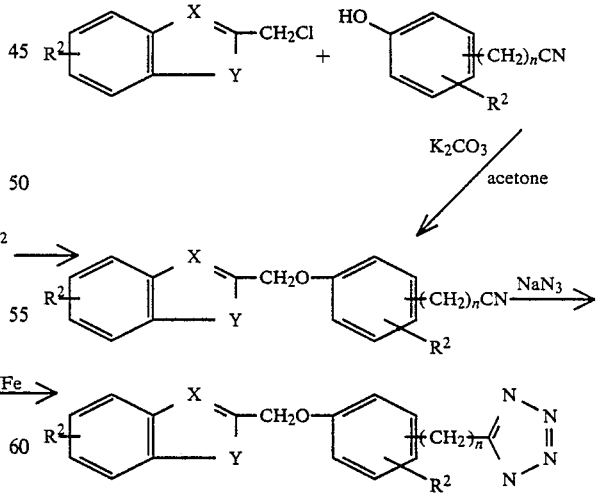

Those compounds in which $R^3$ is lower alkyl can be prepared by alkylating the tetrazole moiety using conventional alkylating agents, such as alkyl halides, alkyl sulfates, alkyl sulfonates and so forth.

Compounds of the invention in which $R^1$ is

can be prepared by the reaction of an appropriate R-, S- or racemic phenylephrine; R-, S- or racemic norphenylephrine; R-, S- or racemic N-ethylphenylephrine; or R-, S- or racemic N-ethylnorphenylephrine derivative with an appropriate benzo-fused heterocyclic derivative as follows:

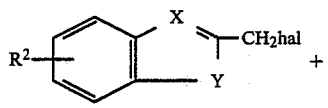

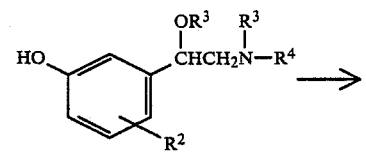

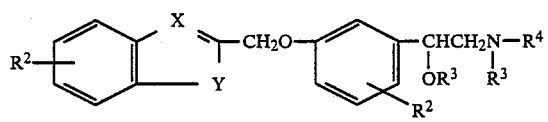

where X, Y, $R^2$, $R^3$ and $R^4$ are as defined hereinbefore and hal refers to a halo radical, for example, chloro or bromo. The reaction is carried out in the presence of cesium carbonate in an organic solvent, for instance acetone, under reflux conditions. The various starting phenylephrine-based derivatives employed in the reaction sequence can be prepared as follows (illustrating preparation of a phenylephrine starting material):

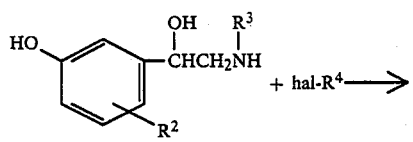

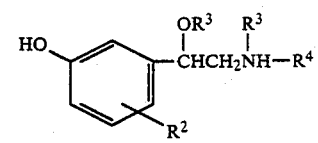

Compounds of the invention in which $R^1$ is

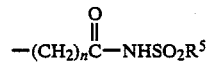

or $-(CH_2)_nCOOR^3$ can be prepared according to two preparative schemes. For those compounds in which $n \geq 2$, the following representative sequence is employed:

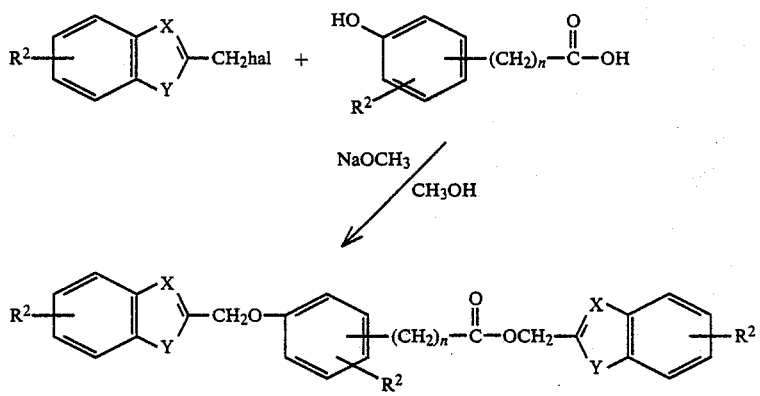

The resulting compounds obtained by this sequence are hydrolyzed to yield intermediate carboxylate acids:

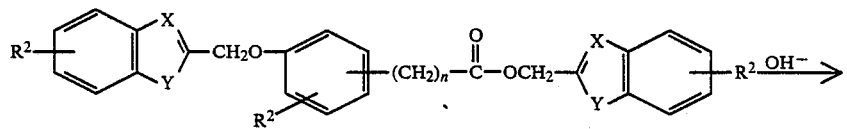

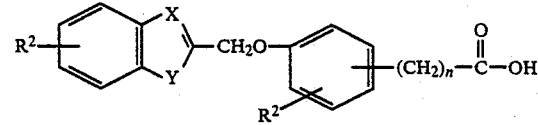

which are then reacted with an appropriate sulfonamide reactant to yield the desired sulfonylcarboxamide derivatives:

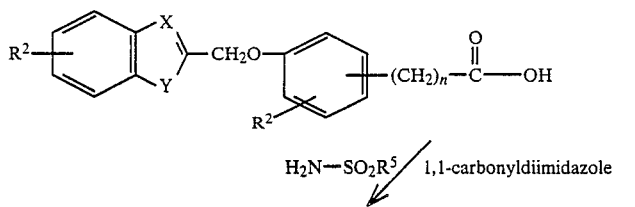

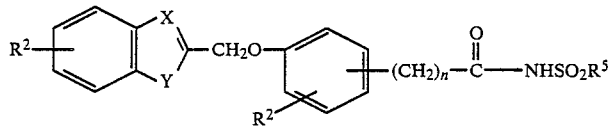

or the carboxylic acid can be esterified to yield the appropriate ester:

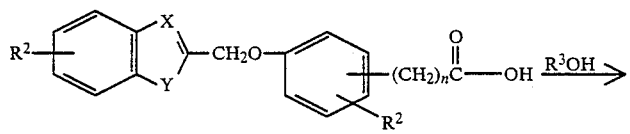

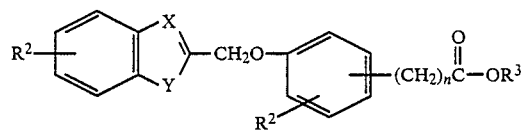

For those compounds in which $R^1$ is $-(CH_2)_nC-OR^3$ or $$-(CH_2)_n\overset{O}{\overset{\|}{C}}-NHSO_2R^5$$

and n is 0 or 1, the following reaction sequence is employed, in which $R^3$ is lower alkyl:

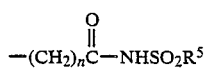 +

-continued

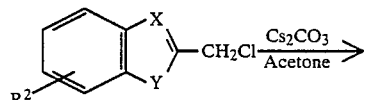

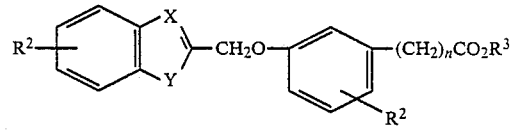

At this point, the carboxylic acid ester compounds can be hydrolyzed to the carboxylic acids, which can then be reacted with the appropriate sulfonamide reactants in order to obtain the desired sulfonylcarboxamide derivatives:

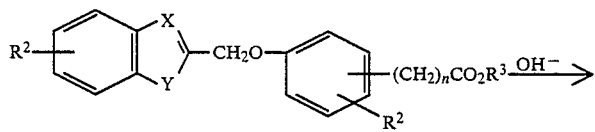

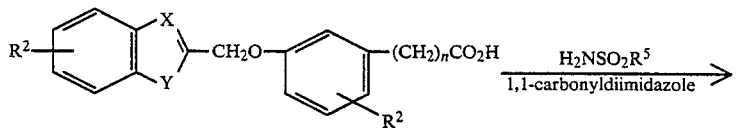

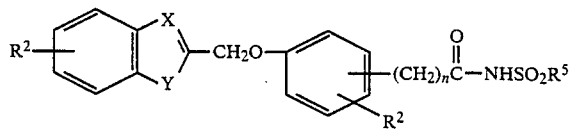

Compounds of the invention in which $R^1$ is

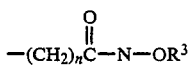

can be prepared using the carboxylic acid ester compounds described in the immediately preceding reaction sequences as starting compounds:

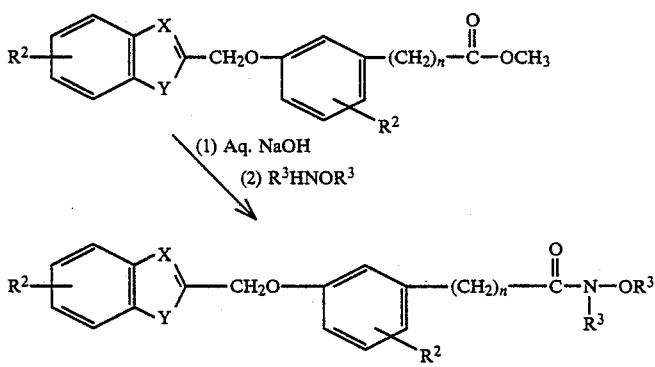

OR

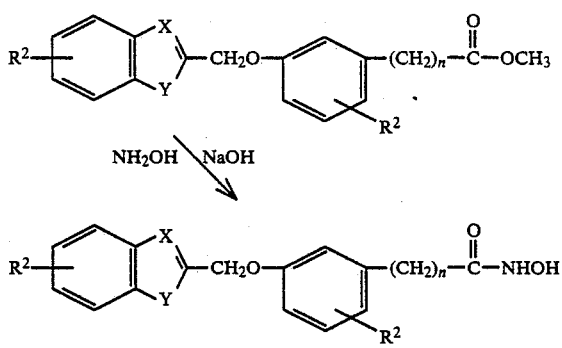

Finally, compounds of the invention in which $R^1$ is

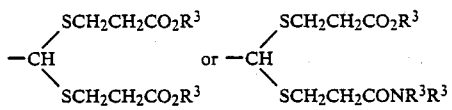

can be prepared by the following reaction sequence:

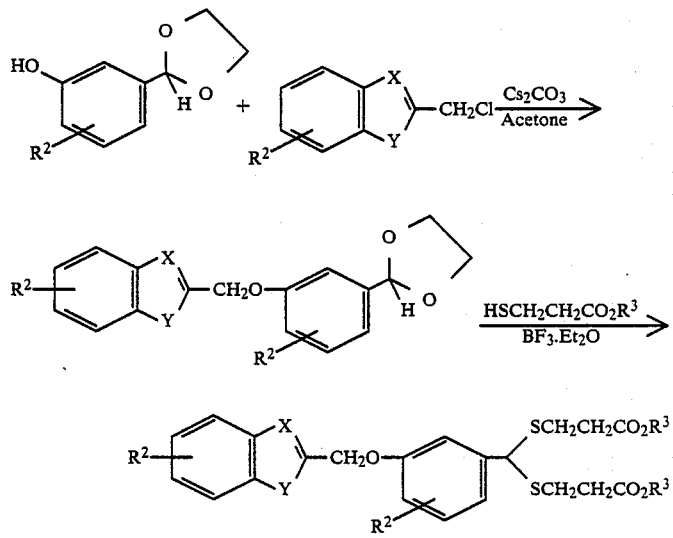

The starting ketal in the above-outlined preparative sequence can be prepared by the reaction of a suitable 3-hydroxybenzaldehyde with ethylene glycol in the presence of p-toluenesulfonic acid:

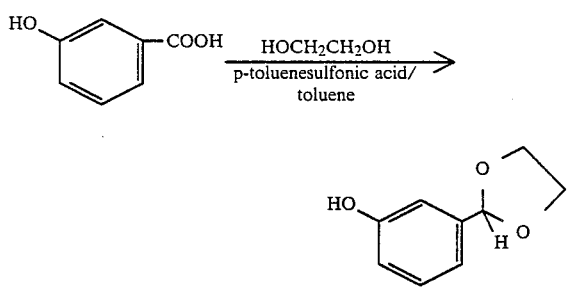

where it is desired to prepare the monoamide derivatives of the above compounds, the following reaction sequence is employed:

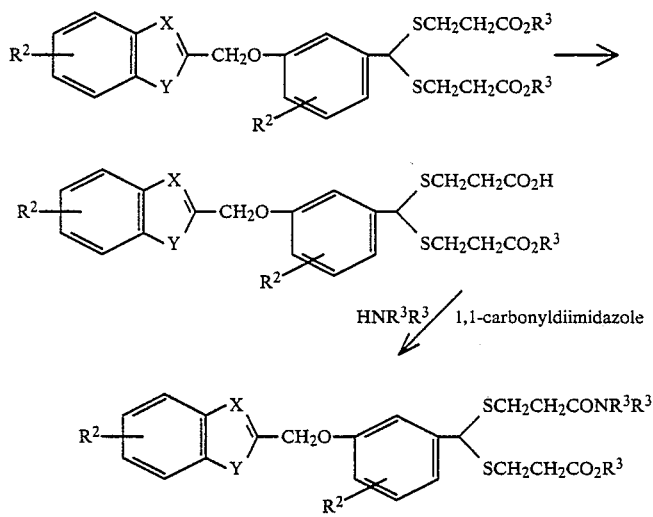

The benzo-fused heterocyclic compounds used as starting material in all the above reaction sequences are either commercially available or can be prepared by methods conventional in the art. Thus, for example, such compounds as 2-chloromethylquinazoline can be prepared according to the method described by Armarego and Smith, *J. Chem. Soc.* (C), 1966, 234, and compounds such as 1-methyl-2-chloromethylbenzimidazole, can be prepared by the following reaction scheme:

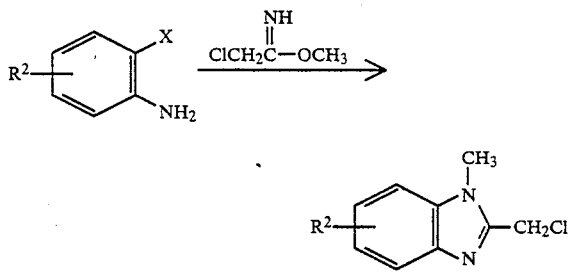

wherein X is NCH$_3$. The reaction is preferably carried out at a controlled low temperature in an organic solvent, such as methylene chloride.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like. The compounds which are carboxylic acids or have a hydroxamic function are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds of the invention, by virtue of their ability to inhibit the activity of lipoxygenase enzyme and to antagonize mediators arising from this enzymatic pathway, are useful in the treatment of inflammatory conditions. Accordingly, the compounds are indicated in the treatment of such diseases as rheumatoid arthritis, osteoarthritis, tendonitis, bursitis and similar conditions involving inflammation. Moreover, by virtue of their ability to inhibit the activity of lipoxygenase enzyme and by their ability to antagonize the effect of LTC$_4$, LTD$_4$ and LTE$_4$ which are the constituents of SRS-A, they are useful for the inhibition of symptoms induced by these leukotrienes. Accordingly, the compounds are indicated in the prevention and treatment of those disease states in which LTC$_4$, LTD$_4$ and LTE$_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders and/or as antiinflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqeuous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE and the cyclooxygenase product $PGE_2$; the ability of the compounds to antagonize $LTD_4$-induced bronchospasm mediated by exogenously administered leukotrienes; and measure the in vivo activity of the compounds as lipoxygenase inhibitors and leukotriene antagonists of endogenous mediators of bronchospasm.

The following examples show the preparation and pharmacological testing of compounds within the invention.

EXAMPLE 1

1,1,1-Trifluoro-N-[3-(2-quinazolinylmethoxy)phenyl]-methanesulfonamide (A) 2-[(3-nitrophenoxy)methyl]quinazoline To a stirred solution of 7 g (0.037 mol) of 2-chloromethylquinazoline[1] and 5.5 g (0.037 mol) of 3-nitrophenol in 150 ml of acetone is added 12 g (0.037 mol) of cesium carbonate and 0.5 g of potassium iodide and the slurry is heated to reflux for 20 hours. The mixture is filtered, and the solution is concentrated in vacuo to obtain a solid residue. The residue is triturated with ethyl acetate to yield 4.4 g (42%) of off-white crystals, m.p. 125°–127° C. Recrystallization from ethyl acetate/pentane gives 2.4 g of crystals, m.p. 128°–129° C.

[1] Prepared according to the procedure of Armarego and Smith, *J. Chem. Soc. (C)*, 1966, 234.

Analysis for: $C_{15}H_{11}N_3O_3$: Calculated: C, 64.05; H, 3.94; N, 14.94. Found: C, 64.10; H, 3.91; N, 14.93.

(B) 3-(2-quinazolinylmethoxy)benzenamine

A suspension of 10 g (0.036 mol) of 2-[(3-nitrophenoxy)methyl]-quinazoline in a solution of 105 g (0.38 mol) of ferrous sulfate heptahydrate and 0.5 ml of concentrated hydrochloric acid in 175 ml of water is heated on a steam bath to 90° C. Concentrated ammonium hydroxide is added in increments of 25 ml, and 3×10 ml over a period of 15 minutes. Heating is discontinued and the reaction mixture is allowed to cool over a period of 45 minutes while vigorously stirring. The reaction mixture is diluted with 500 ml of water/500 ml of ethyl acetate and filtered through Celite. The layers are separated and the ethyl acetate solution is charcoaled, filtered and concentrated to obtain an oil, which is subjected to high pressure liquid chromatography (ethyl acetate/hexane as eluent). Fractions 14–20 are combined and concentrated to obtain 5 g (56%) of off-white crystals, m.p. 103°–7° C.

Analysis for: $C_{15}H_{13}N_3O$: Calculated: C, 71.69; H, 5.21; N, 16.73. Found: C, 71.25; H, 5.08; N, 16.22.

(C)

1,1,1-Trifluoro-N-[3-(2-quinazolinylmethoxy)phenyl]-methanesulfonamide

A solution of 5 g (0.02 mol) of 3-(2-quinazolinylmethoxy)benzenamine and 2.5 g (0.024 mol) of triethylamine in 150 ml of methylene chloride is cooled to −70° C. A solution of 6.2 g (0.022 mol, 3.7 ml) of trifluoromethanesulfonic acid anhydride in 50 ml of methylene chloride is added from a dropping funnel and the mixture is allowed to warm to room temperature. The solution is concentrated in vacuo and the residue is dissolved in 250 ml of ethyl acetate/250 ml of water. The layers are separated and the ethyl acetate solution is washed with brine, dried over magnesium sulfate, and concentrated in vacuo to give 6.8 g of residue, m.p. 140°–150° C. Recrystallization from isopropanol gives 1.7 g (22%) of crystals, m.p. 173°–176° C.

Analysis for: $C_{16}H_{12}F_3N_3O_3S$: Calculated: C, 50.13; H, 3.16; N, 10.96. Found: C, 50.23; H, 3.12; N, 10.59.

EXAMPLE 2

2-[[3-(1H-Tetrazol-5-ylmethyl)phenoxy]methyl]-quinazoline (A) 3-(2-quinazolinylmethoxy)benzenacetonitrile To a solution of 5.5 g (0.0413 mol) of 3-hydroxyphenylacetonitrile and 7.4 g (0.0413 mol) of 2-(choromethyl)quinazoline in 150 ml of acetone is added 10 g (0.03 mol) of cesium carbonate and 0.5 g of potassium iodide and the slurry is heated to reflux for 20 hours. The mixture is filtered and the solution is concentrated in vacuo to obtain a dark residue. The residue is dissolved in hot ethyl acetate, the solution is charcoaled, and concentrated in vacuo to obtain 13 g of an oil, which is subjected to high pressure liquid chromatography (ethyl acetate/hexane as eluent). Fractions 4–8 are combined, and concentrated to recover 2.7 g (37%) of 3-hydroxyphenylacetonitrile, while fractions 12–15 give a residue, which upon trituration with ethyl acetate/pentane gives 2.2 g (19%) of crystals, m.p. 82°–7° C.

Analysis for: $C_{17}H_{13}N_3O$: Calculated: C, 74.16; H, 4.76; N, 15.26. Found: C, 74.57; H, 4.82; N, 15.20.

(B)
2-[[3-(1H-tetrazol-5-ylmethyl)phenoxy]methyl]-quinazoline

To a solution of 6.3 g (0.023 mol) of 3-(2-quinazolinyl-methoxy)benzeneacetonitrile in 150 ml of dimethylformamide are added 7.5 g (0.115 mol) of sodium azide and 6.2 g (0.115 mol) of ammonium chloride, and the slurry is heated to 135° C. for 72 hours. The slurry is poured into 500 ml of water/500 ml of ethyl acetate, and the layers are separated. The aqueous phase is twice extracted with 250 ml of ethyl acetate, and the combined ethyl acetate solution is twice washed with 500 ml of water, dried over anhydrous magnesium sulfate, and concentrated in vacuo to obtain 4 g of crystals, m.p. 129°–131° C. Recrystallization from ethanol gives 2.5 g (34%) of crystals, m.p. 129°–131° C., MS(CI) 319 (M+H).

Analysis for: $C_{17}H_{14}N_6O$: Calculated: C, 64.14; H, 4.43; N, 26.40. Found: C, 63.78; H, 4.53; N, 26.04.

EXAMPLE 3

N,N-Diethyl-N'-[2-hydroxy-2-[3-(2-quinazolinylmethoxy)phenyl]ethyl]-N'-methylurea, ¾ hydrate To a solution of 8 g (0.03 mol) of N,N-diethyl-N'-[2-hydroxy-2-(3-hydroxyphenyl)ethyl]-N'-methylurea and 5.5 g (0.03 mol) of 2-(chloromethyl)quinazoline in 150 ml of acetone are added 10 g (0.03 mol) of cesium carbonate and 0.5 g of potassium iodide and the slurry is heated to reflux for 20 hours. The mixture is filtered and the solution is concentrated in vacuo to obtain an oil. The product is dissolved in ethyl acetate, the resulting solution is charcoaled and concentrated in vacuo to obtain 7 g (55%) of a viscous oil.

Analysis for: $C_{23}H_{28}N_4O_3 \cdot \frac{3}{4}H_2O$: Calculated: C, 65.46; H, 7.04; N, 13.28. Found: C, 65.42; H, 6.97; N, 12.75.

EXAMPLE 4

1,1,1-Trifluoro-N-[[3-(2-quinolinylmethoxy)phenyl]ethyl]methanesulfonamide (A)
1,1,1-Trifluoro-N-[2-(3-methoxyphenyl)ethyl]methanesulfonamide A slurry of 14.1 g (0.075 mol) of 3-methoxyphenylethylamine hydrochloride[1] in a solution of 15 g (0.15 mol) of triethylamine in 200 ml of methylene chloride is cooled to −40° C. A solution of 21.2 g (0.075 mol) of trifluoromethanesulfonic acid anhydride in 100 ml of methylene chloride is added from a dropping funnel and the solution is allowed to warm to room temperature. The solution is concentrated in vacuo to obtain a residue which is stirred in 50 ml of Claisen's alkali for 3 hours at room temperature. The mixture is poured into 500 ml of water, washed with 500 ml of methylene chloride and filtered through Celite. The aqueous solution is acidified to pH 3 with concentrated hydrochloric acid, and extracted twice with 500 ml of methylene chloride. The methylene chloride solution is washed with water, dried over anhydrous magnesium sulfate, and concentrated in vacuo to obtain 12.5 g (59%) of an oil, MS(CI) 284 (M+H). The product is used without further purification in the subsequent step.

[1] Prepared according to the procedure reported in *J. Med. Chem.*, 8, 368 (1965).

(B)
1,1,1-Trifluoro-N-[2-(3-hydroxyphenyl(ethyl]methanesulfonamide

A solution of 12.5 g (0.044 mol) of 1,1,1-trifluoro-N-[2-(3-methoxyphenyl)ethyl]methanesulfonamide in 150 ml of methylene chloride is cooled to −40° C. A solution of boron tribromide in methylene chloride (90 ml, 0.09 mol) is added from a dropping funnel and the mixture is allowed to warm to room temperature. The solution is concentrated in vacuo to obtain a residue, which is rapidly added to 50 ml of methanol. The solution is concentrated in vacuo to obtain 11.8 g (100%) of an oil, MS (CI) 270 (M+H). The product is used without further purification in the subsequent step.

(C)
1,1,1-Trifluoro-N-[[3-(2-quinolinylmethoxy)phenyl]ethyl]methanesulfonamide

To a solution of 11.8 g (0.044 mol) of 1,1,1-trifluoro-N-[2-(3-hydroxyphenyl)ethyl]methanesulfonamide and 8 g (0.044 mol) of 2-(chloromethyl)quinoline in 300 ml of acetone are added 14.5 g (0.044 mol) of cesium carbonate and 1 g of potassium carbonate, and the slurry is heated for 20 hours. The mixture is poured into ice water, acidified to pH 3 with concentrated hydrochloric acid and extracted 3 times with ethyl acetate. The combined ethyl acetate solutions are washed with water, dried over anhydrous magnesium sulfate, and concentrated to obtain 13 g of an oil, which is subjected to high pressure liquid chromatography (ethyl acetate/hexane as eluent). Fractions 13–19 are combined and concentrated to obtain a residue, which is recrystallized from ethyl acetate/pentane to obtain 3.7 g of crystals, m.p. 115° C. Repeated recrystallization from ethyl acetate/pentane gives 2.4 g (13%) of crystals, m.p. 115°–116° C.

Analysis for: $C_{19}H_{17}F_3N_2O_3S$: Calculated: C, 55.60; H, 4.18; N, 6.83. Found: C, 55.68; H, 4.18; N, 6.73.

EXAMPLE 5

N-Ethyl-3-[(1-methyl-2-benzimidazolyl)methoxy]phenyl sulfonamide (A)
3-[(1-methyl-2-benzimidazolyl)methoxy]nitrobenzene A mixture of 1-methyl-2-(chloromethyl)benzimidazole (9.8 g), 3-nitrophenol (7.5 g), cesium carbonate (17.6 g), sodium carbonate (5.7 g), potassium iodide (0.5 g) and acetone (250 ml) is heated at reflux overnight. The mixture is filtered and the resulting solution is partially concentrated. A crystalline solid forms which is filtered and dried, giving 10.8 g (70% yield) of title compound, m.p. 183°–185° C.

(B)
3-[(1-methyl-2-benzimidazolyl)methoxy]benzenamine

To a suspension of 3-[(1-methyl-2-benzimidazolyl)methoxy]nitrobenzene (8 g) in ethanolic hydrochloric acid is added powdered iron. The reaction is stirred overnight at room temperature. After neutralization with saturated aqueous sodium bicarbonate, the mixture is extracted three times with methylene chloride. The extract is dried over magnesium sulfate and concentrated to give 7.2 g (100% yield) of product, m.p. 149°–153° C.

(C)
N-Ethyl-3-[(1-methyl-2-benzimidazolyl)methoxy]phenyl sulfonamide

To a solution of 3-[(1-methyl-2-benzimidazolyl)methoxy]benzenamine (2 g) and triethylamine (0.79 g) in tetrahydrofuran (100 ml) at room temperature is slowly added a solution of ethanesulfonyl chloride (1.0 g) in tetrahydrofuran. The reaction is stirred for 1 hour. The mixture is filtered through a pad of Celite and silica gel and the solvent is removed in vacuo giving an oil. The oil is purified by HPLC and crystallized from hexane to give 1.0 g (37% yield) of product, m.p. 169°–173° C.

Analysis for: $C_{17}H_{19}N_3O_3S$: Calculated: C, 59.11; H, 5.54; N, 12.16. Found: C, 58.87; H, 5.30; N, 12.32.

EXAMPLE 6

Following the procedure of Example 5 and using appropriate starting material and reagents, the following compounds are prepared:

(A)
N-Propyl-3-[(1-methyl-2-benzimidazolyl)methoxy]phenyl sulfonamide, m.p. 151°–153° C.

Analysis for: $C_{18}H_{21}N_3O_3S$: Calculated: C, 60.14; H, 5.88; N, 11.69. Found: C, 60.32; H, 5.76; N, 11.62.

(B)
N-Butyl-3-[(1-methyl-2-benzimidazolyl)methoxy]phenyl sulfonamide, m.p. 154°–159° C.

Analysis for: $C_{19}H_{23}N_3O_3S$: Calculated: C. 59.66; H, 6.32; N, 10.98. Found: C, 59.67; H, 6.09; N, 11.17.

EXAMPLE 7

[[[3-(2-Quinolinyl)phenyl]amino]sulfonyl]acetic acid methyl ester

A solution of 11 g (0.044 mol) of 3-[(2-quinolinyl)methoxy]benzenamine, prepared from 2-(chloromethyl)quinoline using the procedure of Example 5, steps A and B, and 4.5 g (0.044 mol) of triethylamine in 250 ml of methylene chloride is cooled to 0° C. A solution of 7.6 g (0.044 mol) of chlorosulfonylacetic acid methyl ester in 100 ml of methylene chloride is added from a dropping funnel and the mixture is allowed to warm to room temperature. The methylene chloride solution is twice washed with water, dried over anhydrous magnesium sulfate and concentrated to obtain 17 g of an oil, which is subjected to high pressure liquid chromatography (ethyl acetate/hexane as eluent). Fractions 3–9 are combined and concentrated to obtain a residue, which upon trituration with ether gives 11.5 g of crystals. Recrystallization from ethanol gives 6.5 g (37%) of crystals, m.p. 120°–122° C.

Analysis for: $C_{19}H_{18}N_2O_5S$: Calculated: C, 59.05; H, 4.69; N, 7.25; S, 8.30. Found: C, 59.03; H, 4.69; N, 7.16; S, 8.25.

EXAMPLE 8

3-(2-Quinazolinylmethoxy)benzoic acid (A) 3-(2-quinazolinylmethoxy)benzoic acid methyl ester A mixture of 6.00 g (0.03359 moles) of 2-chloromethylquinazoline, 5.11 g (0.03359 moles) of methyl 3-hydroxybenzoate, 10.9 g (0.03359 moles) of cesium carbonate, and 0.100 g (0.602 mmoles) of potassium iodide in 150 ml of acetone is heated at reflux for 4 hours. A further 40 ml of acetone is added and reflux continued for another 4½ hours. The mixture is allowed to stand at room temperature overnight. The acetone is removed in vacuo. After the addition of 200 ml of ethyl acetate the mixture is heated, Norite is added, heating continued and the hot mixture filtered through Celite. The Celite pad is washed with hot ethyl acetate. The combined filtrate and washings are evaporated in vacuo. After unsuccessful attempts to crystallize the residue from ethyl acetate/pentane the mixture is evaporated in vacuo giving 11.42 g of viscous liquid. HPLC on silica gel using hexane/ethyl acetate as eluent gives the title compound as a viscous amber oil which crystallizes on standing in the refrigerator, 6.26 g yellow solid, m.p. 78°–80° C.; IR (KBr) 1712, 1588, 1442, 1293 cm$^{-1}$; NMR (DMSO-d$_6$) 9.71 (s, 1H), 7.35–8.25 (m, 8H), 5.52 (s, 2H), 3.82 (s, 3H).

Analysis for: $C_{17}H_{14}N_2O_3$: Calculated: C, 69.38; H, 4.79; N, 9.52. Found: C, 69.13; H, 4.75; N, 9.47.

(B) 3-(2-quinazolinylmethoxy)benzoic acid

A mixture of 5.50 g (0.01869 moles) of 3-(2-quinazolinylmethoxy)benzoic acid methyl ester, 30.1 ml (0.0301 moles) of 1N sodium hydroxide and 22 ml of tetrahydrofuran is heated at reflux for 50 minutes. The mixture is allowed to come to room temperature and evaporated in vacuo giving a solid residue. After the addition of water and filtration through Celite the filtrate is acidified with 2.4M hydrochloric acid. The resulting precipitate is filtered, washed with water until the washings are pH 6. The precipitate is dried overnight in a vacuum desiccator and azeotroped with toluene on a rotoevaporator. Drying in vacuo gives the title compound, 4.75 g colorless solid, m.p. 221°–224° C.; IR (KBr) 1695, 1576, 1285, 1220 cm$^{-1}$; NMR (DMOS-d$_6$) 9.73 (s, 1H), 7.34–8.22 (8H, aromatic) 5.56 (2H, s), 3.43 (1H, broad).

Analysis for: $C_{16}H_{12}N_2O_3$: Calculated: C, 68.57; H, 4.32; N, 9.99. Found: C, 68.31; H, 4.33; N, 9.91.

EXAMPLE 9

3,3'-[[3-(2-Quinolinylmethoxy)phenyl]methylenebis(thio)]bis propanoic acid methyl ester (A) 1-(1,3-dioxolan-2-yl)-3-hydroxybenzene To a solution of 3-hydroxybenzaldehyde (91.6 g, 0.75 mol) in 500 ml toluene is added ethylene glycol (333.0 g, 5.3 mol) and p-toluenesulfonic acid (0.19 g, 0.001 mol). The flask is equipped with a Dean-Stark trap and the mixture is refluxed for 2 days, extracted with saturated sodium bicarbonate solution and the organic phase separated and dried (MgSO$_4$). Filtration and evaporation of solvent gives the title product as an oil (80.3 g, 64% yield).

(B) 2-[[3-(1,3-dioxolan-2-yl)phenoxy]methyl]quinoline

A solution of the ketal of Step A, above, (10 g, 0.06 mol), 2-chloromethylquinoline (10.6 g, 0.06 mol), cesium carbonate (20.0 g, 0.06 mol) and potassium iodide (0.16 g, 0.001 mol) in 250 ml acetone is refluxed 20 hours. The solution is filtered through Celite and silica gel and the solvent is removed in vacuo. The resulting crude solid is recrystallized using 2-propanol to give 13.7 g of crystalline solid (74% yield) m.p. 67°–69° C.

Analysis for: $C_{19}H_{17}NO_3$: Calculated: C, 74.25; H, 5.57; N, 4.55. Found: C, 74.07; H, 5.58; N, 4.51.

(C)
3,3'-[[3-(2-quinolinylmethoxy)phenyl]methylenebis(thio)bis propanoic acid methyl ester A mixture of the quinoline-ketal intermediate of Step B (3.0 g, 0.009 mol) and methyl-3-mercaptopropionate (2.3 g, 0.0196 mol) is dissolved in methylene chloride, the mixture is cooled to 0° C. and boron trifluoride etherate (2.78 g, 0.0196 mol) is added. After 1 hour the reaction is quenched with distilled water, and the organic phase is dried (MgSO$_4$). Filtration through Celite and silica gel, and solvent removal in vacuo gives the title compound as an oil (2.2 g) 47% yield.

Analysis for: $C_{25}H_{27}NO_5SO_2 \cdot \frac{1}{4}H_2O$: Calculated: C, 61.26; H, 5.65; N, 2.85. Found: C, 61.18; H, 5.53; N, 3.00.

EXAMPLE 10

3,3'-[[3-(2-Quinolinylmethoxy)phenyl]methylene-bis(thio)bis propanoic acid

The title compound is prepared according to the method of Example 9, using 3-mercaptopropanoic acid instead of methyl-3-mercaptopropionate in Step C. The compound is a solid having a melting point of 150°–152° C.

Analysis for: $C_{23}H_{23}NO_5S_2 \cdot \frac{1}{4}H_2O$: Calculated: C, 59.78; H, 5.12; N, 3.03. Found: C, 59.83; H, 5.03; N, 2.61.

EXAMPLE 11

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as LTB$_4$ [see Ford-Hitchinson, *J. Roy. Soc. Med.*, 74, 831 (1981)]. The assay of this Example measures the ability of the compounds of the invention to inhibit the synthesis of 5-HETE by rat glycogen-elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by CO$_2$ asphyxiation and peritoneal cells are harvested by peritoneal lavage using Ca$^{++}$ and Mg$^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing Ca$^{++}$ and Mg$^{++}$ and 10 mM L-cysteine at a concentration of 2×10$^7$ cells/ml. To 1 ml portions of cell suspension, test drugs or vehicle are added and incubated at 37° C. for 10 minutes. Following this preincubation, the calcium ionophore (10 μm), A23187, is added together with 0.5 μCi [$^{14}$C] arachidonic acid and further incubated for 10 minutes. The reaction is stopped by the addition of ice cold water (3 ml) and acidification to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system—hexane:ether:acetic acid (50:50:3). After chromatography, the areas associated with 5-HETE standard are identified by autoradiography, cut out and quantitated by liquid scintillation.

Results are expressed as the 50% Inhibitory concentration.

Testing compounds of the invention in this assay gives the following results:

TABLE I

| Compound of Example Number | 50% Inhibitory Concentration (IC$_{50}$) μm |
|---|---|
| 1 | >10 |
| 4 | 1.8 |

The results show that compounds of this invention have significant activity in inhibiting the synthesis of the arachidonic acid lipoxygenase oxidation product 5-HETE.

EXAMPLE 12

The procedure of Example 11 is also employed for the determination of the ability of the compounds of the invention to inhibit the synthesis of the arachidonic acid cyclooxygenase oxidation product PGE$_2$.

In this assay, the procedure of Example 11 is carried out as described. However, in order to determine cyclooxygenase activity, the samples are cochromatographed with authentic reference PGE$_2$ in the solvent system ethyl acetate:formic acid (80:1) and the upper phase of ethyl acetate:isoctance:acetic acid:water (110:50:20:100). After chromatography, the areas associated with PGE$_2$ standard are identified by autoradiography, cut out and quantitated by liquid scintillation techniques.

The results are calculated as in Example 8 and presented below:

TABLE II

| Compound of Example Number | 50% Inhibitory Concentration (IC$_{50}$) μM |
|---|---|
| 1 | >10 |
| 4 | 11.7 |

The results show that the compounds tested have quite significant activity in inhibiting the synthesis of the arachidonic acid cyclooxygenase oxidation product PGE$_2$.

EXAMPLE 13

The assay of this Example measures the in vivo ability of the compounds of the invention to inhibit the bronchospasm induced in guinea pigs by the exogenously administered leukotrienes C$_4$ and/or D$_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for LTC$_4$ range from 1 to 2 μg/kg and for LTD$_4$ the range is from 0.3 to 1 μg/kg. The aerosol bronchoprovocation dose for LTC₄ is generated from 1.6 μM solution and for LTD₄ from a 2.0 μM solution.

Test drugs are administered either intravenously, intragastrically, by aerosol or orally at 1 or 10 minutes before induction of bronchospasm by administration of either LTC₄ or LTD₄ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3 (1 \min) + 4 (3 \min) + 2 (5 \min)}{10 (\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance (p<0.05). ED₅₀ values can also be determined by inverse prediction from linear regression lines through points between 10 and 90% inhibition.

The results for a compound of the invention are as follows:

TABLE III

| Compound of Example Number | Dose (mg/kg) | % Inhibition | ED₅₀ (mg/kg) |
|---|---|---|---|
| 1 | | | 2.0* |
| | | | 0.5** |
| 2 | 25* | 77 | |
| 3 | 25* | 78 | |
| 4 | 25* | 14 | |
| 7 | 25* | 67 | |
| | 25** | 29 | |
| 8 | 25* | 67 | |
| 9 | 50* | 46 | |
| 10 | 50* | 44 | |

Compound administered at 10 minutes before induction od bronchospasm

\* = intraduodenally administered
\*\* = intragastrically administered

The results show that compounds of the invention have in vivo activity against LTD₄ induced bronchoconstriction.

EXAMPLE 14

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated is artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally, intragastrically or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3 (1 \min) + 4 (3 \min) + 2 (5 \min)}{10 (\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and ED₅₀ doses are interpolated from the regression lines.

The results for a compound of the invention in this assay, using LTD₄ for induction of bronchospasm, are given below:

TABLE IV

Compound administered at 10 minutes before intravenously administered ovalbumin challenge

| Compound of Example Number | Dose mg/kg | % Inhibition |
|---|---|---|
| 1 | 25* | 78 |

TABLE IV-continued

Compound administered at 10 minutes before
intravenously administered ovalbumin challenge

| Compound of Example Number | Dose mg/kg | % Inhibition |
|---|---|---|
| | 25** | 59 |

\* = intraduodenally administered

\*\* = intragastrically administered

The results show that the compound tested has significant in vivo activity in inhibiting ovalbumin induced bronchospasm mediated by endogenous products of the lipoxygenase oxidation of arachidonic acid.

What is claimed is:

1. A compound having the formula

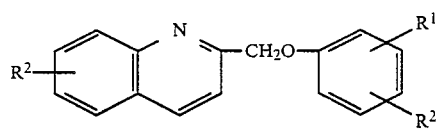

wherein
$R^1$ is

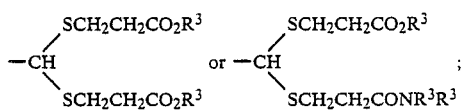

$R^2$ is hydrogen, loweralkyl, loweralkoxy, lower alkoxycarbonyl, trifluoromethyl, nitro, cyano or halo;
$R^3$ is hydrogen or loweralkyl;
and the pharmaceutically acceptable salts thereof.

2. The compound of claim 1, which is 3,3'-[[3-(2-quinolinylmethoxy)phenyl]methylenebis(thio)]bis propanoic acid methyl ester.

3. The compound of claim 1, which is 3,3'-[[3-(2-quinolinylmethoxy)phenyl]methylenebis(thio)]bis propanoic acid.

* * * * *